United States Patent
Eren et al.

(10) Patent No.: US 10,087,474 B2
(45) Date of Patent: Oct. 2, 2018

(54) METHOD FOR PRODUCING BACTERIOCHLOROPHYLL A

(71) Applicant: TOOKAD IP SARL, Luxembourg (LU)

(72) Inventors: Doron Eren, Neta'im (IL); Nitsa Mazor, Kibbutz Sde Boker (IL)

(73) Assignee: TOOKAD IP SARL, Luxembourg (LU)

( * ) Notice: Subject to any disclaimer, the term of this patent is extended or adjusted under 35 U.S.C. 154(b) by 224 days.

(21) Appl. No.: 14/774,665

(22) PCT Filed: Mar. 11, 2014

(86) PCT No.: PCT/IB2014/000468
§ 371 (c)(1),
(2) Date: Sep. 10, 2015

(87) PCT Pub. No.: WO2014/140786
PCT Pub. Date: Sep. 18, 2014

(65) Prior Publication Data
US 2016/0024542 A1 Jan. 28, 2016

Related U.S. Application Data

(60) Provisional application No. 61/776,314, filed on Mar. 11, 2013.

(51) Int. Cl.
*C12P 17/16* (2006.01)
*C12P 17/18* (2006.01)

(52) U.S. Cl.
CPC ........... *C12P 17/165* (2013.01); *C12P 17/182* (2013.01)

(58) Field of Classification Search
None
See application file for complete search history.

(56) References Cited

U.S. PATENT DOCUMENTS 5,935,808 A * 8/1999 Hirschberg ............. C12P 23/00
435/252.1

OTHER PUBLICATIONS

Robert J. Porra et al. "Biosynthesis of the 3-Acetyl and 131-Oxo Groups of Bacteriochlorophyll a in the Facultative Aerobic Bacterium, Rhodovulum sulfidophilum. The presence of both oxygenase and hydratase pathways for isocyclic ring formation", European Journal of Biochemistry, vol. 257, No. 1, Oct. 1, 1998 (Oct. 1, 1998), pp. 185-191.
Urakami T. et al. "Production of ubiquinone and bacteriochlorophyll a by Rhodobacter sphaeroides and Rhodobacter sulfidophilus", Journal of Fermentation and Bioengineering, Society of Fermentation Technology, JP, vol. 76, No. 3, Jan. 1, 1993 (Jan. 1, 1993), pp. 191-194.
Shioi, Yuzo. Growth Characteristics and Substrate Specificity of Aerobic Photosynthetic Bacterium, *Erythrobacter* Sp. (OCh 114), Plant Cell Phisiol. 27(3):567-572, 1986.
International Search Report issued in PCT/IB2014/000468, dated Jul. 9, 2014.

* cited by examiner

*Primary Examiner* — Jennifer M. H. Tichy
(74) *Attorney, Agent, or Firm* — Knobbe, Martens, Olson & Bear, LLP

(57) ABSTRACT

A fed-batch fermentation method is for production of bacteriochlorophyll a (Bchla) from *Rhodovulum sulfidophilum*. The growth medium contains an inorganic nitrogen compound as a nitrogen source. During fermentation, the growth medium is supplemented with a succinate carbon source, an inorganic compound nitrogen source and a phosphorous source from external reservoirs connected to the fermenter vessel. After completion of the fermentation, Bchla is recovered from the separated cells.

7 Claims, No Drawings

METHOD FOR PRODUCING BACTERIOCHLOROPHYLL A

CROSS REFERENCE TO RELATED APPLICATIONS

This application is the U.S. National Phase of International Application No. PCT/IB2014/000468, filed Mar. 11, 2014, designating the U.S. and published in English as WO 2014/140786 on Sept. 18, 2014 which claims the benefit of U.S. Provisional Patent Application No. 61/776,314, filed Mar. 11, 2013.

FIELD OF THE INVENTION

The present invention is directed in general to methods of producing bacteriocholorophylls from microorganisms and, in particular, to improved fermentation methods for production of bacteriocholorophyll a from purple bacteria.

BACKGROUND OF THE INVENTION

Photodynamic therapy (PDT) is used as a non-surgical treatment of tumors. It combines non-toxic drugs and non-hazardous photosensitizing illumination, both innocuous agents by themselves, to generate, in the presence of molecular oxygen, cytotoxic reactive oxygen species (ROS) in situ which can kill or inactivate cells. Being a binary treatment modality, PDT allows for greater specificity and has the potential of being more selective, yet not less destructive, when compared with commonly used chemotherapy or radiotherapy.

Porphyrins have been employed as the first generation photosensitizing agents in clinics. Porfimer sodium (Photofrin®, a trademark of Axcan Pharma Inc.), the world's first approved photodynamic therapy agent, which is obtained from hematoporphyrin-IX by treatment with acids and has received FDA approval for treatment of esophageal and endobronchial non-small cell lung cancers, is a complex and inseparable mixture of monomers, dimers, and higher oligomers.

Large amount of work has been devoted to the synthesis of single pure compounds—so-called "second generation" sensitizers—which absorb at long wavelength, have well established structures and exhibit better differentiation between their retention in tumor cells and their retention in skin or other normal tissues. In order to optimize the performance of the porphyrin drugs in therapeutics and diagnostics, several porphyrin derivatives have been proposed in which, for example, there is a central metal atom (other than Mg) complexed to the four pyrrole rings, and/or the peripheral substituents of the pyrrole rings are modified and/or the macrocycle is dihydrogenated to chlorophyll derivatives (chlorins) or tetrahydrogenated to bacteriochlorophyll derivatives (bacteriochlorins).

Due to their intense absorption in favourable spectral regions (650-850 nm) and their ready elimination after treatment, chlorophyll (Chl) and bacteriochlorophyll (Bchl) derivatives have been identified as excellent sensitizers for PDT of tumors, having superior properties in comparison to porphyrins. Bacteriochlorophylls are of potential advantage compared to the chlorophylls because they show intense near-infrared bands, i.e., at considerably longer wavelengths than chlorophyll derivatives.

Bacteriochlorophylls are photosynthetic pigments that occur in various phototrophic bacteria. They are related to chlorophylls, which are the primary pigments in plants, algae, and cyanobacteria. Bacteria that contain bacteriochlorophyll (Bchl) conduct photosynthesis, but do not produce oxygen. They use wavelengths of light not absorbed by plants or Cyanobacteria. Different groups of bacteria produce different types of bacteriochlorophyll:

| Pigment | Bacterial group | In vivo infrared absorption maximum (nm) |
|---|---|---|
| Bchl a | Purple bacteria (Proteobacteria); Chloracidobacterium thermophilum | 805, 830-890 |
| Bchl b | Purple bacteria | 835-850, 1020-1040 |
| Bchl c | Green sulfur bacteria; Chloroflexi; C. thermophilum | 745-755 |
| Bchl cs | Chloroflexi | 740 |
| Bchl d | Green sulfur bacteria | 705-740 |
| Bchl e | Green sulfur bacteria | 719-726 |
| Bchl g | Heliobacteria | 670, 788 |

Chemically, bacteriochlorophylls a, b, and g are bacteriochlorins, meaning their molecules have a bacteriochlorin macrocycle ring with two reduced pyrrole rings (B and D). Bacteriochlorophyll a (herein Bchla) is a compound of the formula:

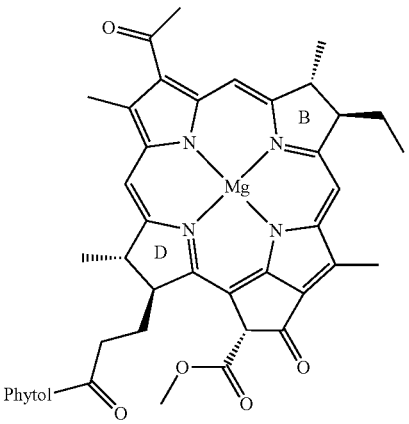

Bacteriochlorophylls c, d and e are chlorins, meaning their molecules have a chlorin macrocycle ring with only one reduced pyrrole ring (D).

Purple Photosynthetic Bacteria

The purple photosynthetic bacteria are able to derive their cellular energy from light, organic compounds or inorganic compounds, depending on the chemical and physical environment. This remarkable versatility usually means that one mode of metabolism is utilized at a time so as to prevent unnecessary biosynthesis of alternative energy systems. Thus, photosynthetic metabolism and hence pigment biosynthesis only occurs under a limited set of conditions.

In regard to their ability to produce bacteriochlorophyll there appear to be two main groups within the purple bacteria. The first group includes Rhodobacter (Rba.) spheroidedes, Rba. Capsulatus and Rhodospirilum rubrum, which photosynthesize and thus produce bacteriochlorophyll anaerobically in the light; they can also synthesize significant amounts of pigment in the dark, but only under low aeration conditions. This indicates an oxygen and light dependent control over the genes encoding the enzymes involved in the synthesis of these pigments. The second group, which includes Rhodovulum sulfidophilum, sp. and

*Rubrivivax* (*Rvi.*) *gelatinosus*, is able to synthesize pigments in the dark and to photosynthesize under both anaerobic and aerobic conditions.

The biosynthesis of Bchla in the facultative aerobic bacterium *Rhodovulum sulfidophilum*, formerly known as *Rhodobacter sulfidophilus*, was described by Porra et al., 1998 (Porra, R J, M. Urzinger, J. Winkler, C. Bubenzer, and H. Scheer, Eur. J. Biochem. 257, 185-191).

Bchla obtained from *Rhodovulum sulfidophilum* has served as the basis for further derivation and modification to produce improved Bchla derivatives employed in PDT and vascular-targeted PDT (VTP) of tumors and other pathological conditions as disclosed, for example, in U.S. Pat. No. 6,147,195, EP 863903, U.S. Pat. Nos. 6,333,319, 6,569,846, WO 2004/045492 and U.S. Pat. No. 8,207,154.

The use of Bchla derivatives for PDT and PDT research is increasing; therefore, there is a growing need to produce higher amounts of Bchla by fermentation.

SUMMARY OF THE INVENTION

The present invention provides a fermentation method for producing bacteriochlorophyll a (Bchla) from the photosensitizing purple bacteria *Rhodovulum sulfidophilum*, comprising the steps of growing the bacteria in a bioreactor and extracting the produced Bchla from the harvested bacteria.

In particular, the present invention relates to a fed-batch fermentation method for production of bacteriochlorophyll a (Bchla) from *Rhodovulum sulfidophilum*, said method comprising:

(i) culturing *Rhodovulum sulfidophilum* in a fermenter vessel in a growth medium containing an inorganic nitrogen compound as the nitrogen source, a carbon source, a phosphorous source, an iron source, a magnesium source, yeast extract and NaCl;

(ii) submitting the culture to a fed-batch fermentation while feeding to the medium a succinate carbon source, an inorganic compound nitrogen source and a phosphorous source from external reservoirs connected to the fermenter vessel and keeping the oxygen level at or lower than 10%;

(i) removing the cells from the medium; and (ii) separating and recovering Bchla from the cells from step (iii).

DETAILED DESCRIPTION OF THE INVENTION

In methods described in the literature, Bchla was obtained from bacteria grown in a medium containing an organic nitrogen source such as peptone, polypeptone or a mixture of amino acids and small peptides obtained by acid hydrolysis of casein known as casamino acids (Shioi, Yuzo, Plant Cell Phisiol. 27(3): 567-572, 1986; Porra et al., Eur. J. Biochem. 257, 185-191, 1998).

It has been found now, in accordance with the present invention, that certain modifications of the fermentation process for growing the purple bacteria *Rhodovulum sulfidophilum* resulted in a 12-fold increase of Bchla volumetric yield improvement and substantially reduced production costs.

Thus, in a main aspect, the present invention provides a fermentation method for producing Bchla from cultured *Rhodovulum sulfidophilum* in amounts significantly exceeding the amounts produced using the known fermentation processes.

As used herein, the terms "fermenter", "fermenter vessel" and "bioreactor" are used interchangeably to denote the vessel in which the growth and fermentation of *Rhodovulum sulfidophilum* occurs according to the present invention.

As used herein, the terms "growth medium" and "fermentation medium" are used interchangeably to denote the medium in which the *Rhodovulum sulfidophilum* bacteria are grown inside the fermenter.

The method of the invention involves improvements both in the bacterium growth medium and in the fermentation process.

The improvement related to the growth medium according to the present invention consists in the replacement of the expensive, animal-derived nitrogen source peptone with an inorganic nitrogen source.

The improvement of the fermentation method according to the present invention comprises continuous supply to the bioreactor of fresh nutrients from external reservoirs containing feed solutions of the nitrogen, carbon and phosphor sources while monitoring on-line the levels of the essential nutrients in the fermentation medium and supplying them as needed. According to this technique, known as "fed-batch fermentation", the nutrients are continuously supplied to the growing bacteria in the bioreactor in amounts and administration rates that depend on the rate these nutrients are consumed in the bioreactor by the bacteria during the fermentation process.

Although inorganic nitrogen sources are sometimes used in bacteria growth medium, the inventors have unexpectedly found that using ammonium chloride as the sole nitrogen source and the fed-batch fermentation method of the invention yielded 350% increase in cell dry weight per liter and 335% increase in Bchla concentration in the cells, namely, 600 mg Bchla per liter—almost 12 times higher than in known commercial processes. In addition, it led to a reduction of about 15% of the cost of the medium commonly used for growing *Rhodovulum sulfidophilum*.

Thus, the present invention relates to a fed-batch fermentation method for production of bacteriochlorophyll a (Bchla) from *Rhodovulum sulfidophilum*, said method comprising:

(i) culturing *Rhodovulum sulfidophilum* in a fermenter vessel in a growth medium containing an inorganic nitrogen compound as the nitrogen source, a carbon source, a phosphorous source, an iron source, a magnesium source, yeast extract and NaCl;

(ii) submitting the culture to a fed-batch fermentation while feeding to the medium a succinate carbon source, an inorganic compound nitrogen source and a phosphorous source from external reservoirs connected to the fermenter vessel and keeping the oxygen level at or lower than 10%;

(iii) removing the cells from the medium; and (iv) separating and recovering Bchla from the cells from step (iii).

The inorganic nitrogen compound in the growth medium can be any of the inorganic nitrogen compounds used in bacteria growth media such as, but not limited to, ammonium chloride, ammonium sulfate, ammonium nitrate, ammonium dihydrogen phosphate, ammonium hydrogen phosphate, potassium nitrate, and sodium nitrate, or any combination thereof. In certain embodiments, the preferred inorganic nitrogen compound is ammonium chloride ($NH_4Cl$). The inorganic nitrogen source is also is supplied to the growing bacteria by supplementing the fermentation medium during the feed-batch fermentation as needed.

The carbon source in the growth medium may be, for example, mono- or disaccharides, sucrose, dicarboxylic acids such as malic acid, succinic acid and sodium succinate, glycerol, citric acid, or any combination thereof. In addition, carbon source comprising succinic acid and sodium succinate is supplied to the growing bacteria by supplementing the fermentation medium during the feed-batch fermentation as needed.

The phosphorous source in the growth medium may comprise one or more water soluble salts of hydrogen phosphate and dihydrogen phosphate such as sodium, potassium, and ammonium phosphates, as well as pyrophosphate. In certain embodiments, the phosphorous source comprises a mixture of the phosphate salts $K_2HPO_4*3H_2O$ and $KH_2PO_4$. In addition, phosphorous source comprising these two phosphate salts is supplied to the growing bacteria by supplementing the fermentation medium during the feed-batch fermentation as needed.

The iron source in the fermentation medium may be one or more water soluble ferric or ferrous salts such as ferric ammonium citrate, ferrous chloride, ferrous acetate and ferrous sulphate. In certain embodiments, the iron source is ferric ammonium citrate ($FeNH_4$citrate).

The magnesium source in the fermentation medium may be one or more water soluble magnesium salts such as magnesium chloride, magnesium gluconate, magnesium nitrate, magnesium sulfate, magnesium citrate, magnesium acetate or magnesium succinate. In certain embodiments, the magnesium source is magnesium sulfate ($MgSO_4*7H_2O$).

The fermentation medium of *Rhodovulum sulfidophilum* may comprise, according to the present invention, a carbon source in the amount of 30-45 g/L, a phosphorous source in the amount of 0.4-0.7 g/L, a nitrogen source in the amount 1.5-3.0 g/L, yeast extract in the amount of 1.5-2.5 g/L, an iron source in the amount of 0.5-1.0 g/L, a magnesium source in the amount of 0.15-0.3 g/L, NaCl in the amount of 10-30 g/L and trace elements.

In certain embodiments, the fermentation medium comprises a mixture of the following ingredients: citric acid, $CaCl_2*2H_2O$, $MgSO_4*7H_2O$, $FeNH_4$citrate, succinic acid, disodium succinate*$6H_2O$, $Na_2SO_4$, $K_2CO_3$, yeast extract, $NH_4Cl$, $KH_2PO_4$, $K_2HPO_4*3H_2O$, NaCl, NaOH, KOH, anti-foam agent and trace elements. The trace elements may be $CoCl_2*6H_2O$, $NiCl_2*6H_2O$, $CuCl_2*2H_2O$, $MnCl_2*4H_2O$, $ZnSO_4*7H_2O$, $Na_2MoO_4*2H_2O$, $H_3BO_3$ and KI, and the antifoam agent may be any antifoam agent used in fermentation methods such as Y-30 or Biospumex.

In certain embodiments, the fermentation medium comprises the following amounts of the following ingredients: 30.0-40.0 g/L succinic acid; 2.0-4.0 g/L $Na_2SO_4$; 0.5-1.0 g/L $CaCl_2$; 0.2-0.5 g/L $K_2CO_3$; 0.5-1.0 g/L ferric ammonium citrate; 1.5-2.5 g/L yeast extract; 3.0-6.0 g/L citric acid; 0.15-0.3 g/L $MgSO_4$; 10-30 g/L NaCl; 1.5-3.0 g/L $NH_4Cl$; 0.2-0.4 g/L $KH_2PO_4$; and 2.0-3.0 g/L $K_2HPO_4$.

During the fed-batch fermentation method, solutions of carbon, nitrogen and phosphorous sources, sometimes referred to herein also as "feed material", are placed each in an external reservoir connected to the fermenter vessel. The carbon source, herein referred to as "succinate carbon source", is an aqueous solution of succinic acid and disodium succinate; the inorganic compound nitrogen source is preferably an aqueous solution of $NH_4Cl$; and the phosphorous source is an aqueous solution of $KH_2PO_4$ and $K_2HPO_4*3H_2O$.

Carbon levels are monitored throughout the fermentation process, and whenever the level of succinic acid in the medium comes to a certain threshold level, for example 1-2 g/L, succinic acid is added (pumped from) to the fermenter from the external reservoir.

Phosphorous levels are monitored throughout the fermentation process, and fresh phosphorous source is added as needed. In certain embodiments, fresh phosphate solution is pumped from the external reservoir into the fermenter as early as 16 hours after fermentation commenced and then further added every 24 hours period.

Ammonia levels are monitored throughout the fermentation process, and fresh nitrogen source is added as needed. In certain embodiments, fresh ammonia solution ($NH_4Cl$ 5N) is pumped from the external reservoir into the fermenter as early as 16 hours after fermentation commenced and then further added every 12 hours period.

The volume of feed materials should minimize as much as possible so succinate solution can be added to extend the course of the fermentation, as needed. At the beginning of the fermentation, since pH rises up to 8.6, sulfuric acid is used to maintain pH=7. During fermentation, NaOH solution is added to maintain pH=7. During this time, the amount of succinic acid is checked, and when it comes to the amount of 1-2 g/L, succinic acid should be added from the external reservoir (instead of sulfuric acid).

The fermentation medium in the fermenter is prepared as follows: forming in the fermenter vessel an initial fermentation medium by preparing a solution (hereinafter "Solution 4") by adding to an aqueous solution of citric acid, $CaCl_2*2H_2O$, $MgSO_4*7H_2O$ and $FeNH_4$citrate (hereinafter "Solution 1") an aqueous solution of succinic acid, $Na_2SO_4$, $K_2CO_3$ and yeast extract (hereinafter "Solution 2"), followed by addition of NaCl, mixing, and addition of a solution of $NH_4Cl$ (hereinafter "Solution 3"), and adjusting the pH to 5 using 10N NaOH, followed by adding to Solution 4 an aqueous solution of an anti-foam agent, closing the fermenter and sterilizing by autoclaving (121° C., 20 min), and further adding to the sterile medium an aqueous solution of the trace elements $CoCl_2*6H_2O$, $NiCl_2*6H_2O$, $CuCl_2*2H_2O$, $MnCl_2*4H_2O$, $ZnSO_4*7H_2O$, $Na_2MoO_4*2H_2O$, $H_3BO_3$ and KI, followed by addition of an aqueous solution of the phosphate salts $KH_2PO_4$, $K_2HPO_4*3H_2O$. An inoculum of *Rhodovulum sulfidophilum* is added to this initial fermentation medium in the fermenter and, during fermentation, fresh amounts of the succinate carbon source, of the ammonium chloride nitrogen source and of the phosphate source are added to the fermentation medium as needed.

The temperature in the fermenter before adding the inoculum of *Rhodovulum sulfidophilum* should be of about 28° C. and the pH=7 (adjusted with NaOH and succinate solution as required).

During fermentation, good agitation and aeration should be maintained, and the temperature, the pH, the oxygen level and the supply of nitrogen, carbon and phosphorus should be monitored. The temperature should be maintained at a minimum of 25° C. and a maximum of 31° C. and the pH control limits are 6.8 and 7.3.

It is very important to keep oxygen at or below 10% after about 10-20 hours of fermentation. A high concentration of oxygen speeds up the growth of the bacteria, but they do not produce bacteriochlorophyll a, while a concentration of 10% of oxygen speeds up bacteriochlorophyll a production.

The fermentation is continued until the volume of the fermentation medium in the vessel increases to about its full capacity.

Once the fermentation is completed, the broth is centrifuged, the supernatant is discarded, the cells are lyophilized and Bchla is extracted from the dried cells. The Bchla can be purified and used for chemical derivation to bacteriochlorophyll derivatives of interest.

The invention will now be illustrated by the following non-limitative examples.

EXAMPLES

Material and Methods

*Rhodovulum sulfidophilum* (DSM Strain 1374) was obtained from the Deutsche Sammlung von Mikroorganismen and Zellkulturen (DSMZ), Braunschweig, Germany.

BioFlo IV 20 L fermenter was from New Brunswick Scientific (USA).

Succinic acid, disodium succinate*6H$_2$O, NH$_4$Cl, FeNH$_4$ citrate/citric acid, K$_2$HPO$_4$, MgCl$_2$ CoCl$_2$*6H$_2$O, NiCl$_2$*6H$_2$O, CuCl$_2$*2H$_2$O, MnCl$_2$*4H$_2$O, ZnSO$_4$*7H$_2$O and KI were purchased from Acros Organics (Geel, Belgium); KH$_2$PO$_4$, Na$_2$SO$_4$, KCl, CaCl$_2$*2H$_2$O, K$_2$CO$_3$, NaHCO$_3$ MgSO$_4$*7H$_2$O and NaCl were purchased from Fisher (Fisher Scientific, Loughborough, UK); casein peptone and casein hydrolysate were purchased from Difco (Lawrence, Kans., USA); yeast extract was purchased from Difco and Bio Springer (Montreal, Quebec, Canada); NH$_4$Cl was purchased from Fluka (Sigma-Aldrich, Rehovot, Israel); KH$_2$PO$_4$ was purchased from Merck (Merck KGaA, Darmstadt Germany); KOH, H$_3$BO$_3$, Y-30 antifoam and Na$_2$MoO$_4$*2H$_2$O were purchased from Sigma (Sigma-Aldrich, Rehovot, Israel).

Example 1

Preparation of a Working Cell Bank of *Rhodovulum sulfidophilum* Bacteria

*Rhodovulum sulfidophilum* bacteria (DSM Strain 1374) were sown on Petri dishes pre-coated with a growth substrate containing agar mixed with aqueous medium prepared from the following ingredients: succinic acid (9 g). Na$_2$SO$_4$ (3 g), KCl (750 mg), CaCl$_2$ (750 mg), NaHCO$_3$ (300 mg), FeNH$_4$ citrate (150 mg), Yeast extract (3 g), Casein peptone (1.5 g), Casein hydrolysate (1.5 g), MgCl$_2$ (7.5 g), NaCl (30 g), deionized water (1500 ml).

The pH of the medium was adjusted to 7 using NaOH 10N and HCl 1M. Agar was added to the medium (7.5 g agar per 500 ml medium) to obtain the growth substrate. Petri dishes coated with the growth substrate were sterilized by autoclaving (121° C., 30 min) and the bacteria were seeded thereon.

After incubation at 30° C. for three days, an inoculum of the bacteria is transferred to a 250 ml Erlenmeyer flask and grown in inoculation medium in which the organic nitrogen source casein peptone (used for bacteria growth in Petri dishes) was replaced with the inorganic source ammonium chloride. The bacteria were grown until the optic density (OD 540 nm) of the culture reached a value above 10. Eight ml aliquots of the inoculum source were transferred to 15 ml sterile cryogenic freezing tubes, 2 ml of 50% sterile glycerol solution were added and the tubes were stored at −80° C. until use.

Example 2

Solutions for the Fermentation Medium and their Preparation

The following solutions were prepared:

Solution 1. The following ingredients were added in the order below and dissolved in 4.5 L deionized water in the fermenter vessel:

| Ingredient | Quantity (g) |
| --- | --- |
| Citric acid | 30 |
| CaCl$_2$*2H$_2$O | 5 |
| MgSO$_4$*7H$_2$O | 15 |
| FeNH$_4$citrate | 0.5 |

Solution 2. The following ingredients were added in the order below and dissolved in 400 ml warm water and deionized water was added to complete 0.5 L:

| Ingredient | Quantity |
| --- | --- |
| Succinic acid | 30 g |
| Na$_2$SO$_4$ | 15 g |
| K$_2$CO$_3$ | 2.5 g |
| Yeast Extract | 30 g |

Solution 3 Ammonium chloride 5N—NH$_4$Cl (about 268 g) was dissolved in 900 ml water and volume completed to 1 L. A sample of 80 ml was transferred to a 100 ml bottle for addition to the fermenter as Solution 3 and the remainder was transferred to a 1 L bottle labeled as Solution 3 for use as nitrogen source reserve during fermentation. Both bottles were sterilized in an autoclave (121° C., 20 min).

Solution 4 was formed in the fermenter by adding 450 ml of Solution 2 to the 4.5 L Solution 1 already in the fermenter vessel, followed by addition of 170 g NaCl and mixing, and then addition of 80 ml Solution 3 (NH$_4$Cl 5N, 1 g NH$_4$$^+$ in liter media). The pH was adjusted to 5 using 10 N NaOH.

Solution 5, the trace elements solution (TES), contained the following ingredients: CoCl$_2$*6H$_2$O (about 50 mg), NiCl$_2$*6H$_2$O (about 50 mg), CuCl$_2$*2H$_2$O (about 100 mg), MnCl$_2$*4H$_2$O (about 150 mg), ZnSO$_4$*7H$_2$O (about 200 mg), H$_3$BO$_3$ (about 1000 mg), Na$_2$MoO$_4$*2H$_2$O) (about 50 mg), and KI (about 500 mg) in 0.5 L water. Aliquots of 35 ml solution 5 were transferred to 100 ml bottles and sterilized by autoclaving (121° C., 20 min).

Solution 6, the phosphate salts solution, was prepared by dissolving 30 g KH$_2$PO$_4$ and 5 g K$_2$HPO$_4$ in 250 ml deionized water. The pH was adjusted to 7 using 10N KOH solution. An aliquot of 55 ml was transferred to a 100 ml bottle and labeled as solution 6 for addition to the fermenter. The remainder was transferred to a 500 ml bottle and labeled as solution 6 for use as phosphorus source reserve during fermentation. Both bottles were sterilized in an autoclave (121° C., 20 min).

Solution 7, the antifoam solution, was prepared by adding about 25 mg of silicon-based antifoam Y-30 to deionized water to a final volume of 250 ml, followed by sterilization in an autoclave (121° C., 20 min), or adding the antifoam Biospumex such that its concentration in the basic fermentation medium ranges from 0.2 to 0.5 mL/L. Generally, the quantity of antifoam introduced into the fermenter is dictated by the amount of foam formed in the medium.

Solution 8, the succinate solution serving as the carbon source as well as pH adaptor, was prepared by dissolving 250 g disodium succinate in 4 L deionized water, adding 450 g succinic acid, warming to dissolve it and then adding deionized water to a final volume of 5 L, followed by sterilization of the solution by autoclaving (121° C., 20 min).

Solution 9, NaOH 10N, was prepared by placing 250 ml deionized water in a 500 ml bottle, sterilizing by autoclaving (121° C., 20 min), adding 100 g NaOH to the cooled bottle and mixing.

Example 3

Fed-Batch Fermentation for Production of Bchla

The pH electrode was calibrated and connected to the fermenter vessel. The DO (dissolved oxygen) electrode was connected to the vessel. Two ml of antifoam were added to Solution 4 at pH 5 in the fermenter vessel just before its closure, and sterilization was set to a cycle of 25 minutes.

The initial fermentation medium contained the following ingredients:

| Ingredient | Concentration |
|---|---|
| Citric acid | 3.0-6.5 g/L |
| $CaCl_2*2H_2O$ | 0.5-1.2 g/L |
| $MgSO_4*7H_2O$ | 1.5-3.5 g/L |
| Ferric ammonium citrate | 50-100 mg/L |
| Succinic acid | 30.0-60.0 g/L |
| $Na_2SO_4$ | 2.0-4.0 g/L |
| $K_2CO_3$ | 0.2-0.5 g/L |
| Yeast extract | 3.0-6.5 g/L |
| $NH_4Cl$ | 1.5-4.0 g/L |
| $KH_2PO_4$ | 1.5.0-3.0 g/L |
| $K_2HPO_4$ | 0.2-0.5 g/L |
| NaCl | 25.0-45.0 g/L |
| Trace element solution | 4.0-7.5 mL/L |
| Antifoam | as needed |

This medium was prepared is several steps, wherein an initial fermentation medium was first prepared in the bioreactor and the other ingredients were added upon initiation of the fermentation process from feed solutions in external reservoirs connected to the bioreactor, and then continuously during fermentation, subsequent to on-line monitoring the nutrient levels in the growth medium. The phosphorous feed solution contained $KH_2PO_4$ (12.0-14.5 g/L) and $K_2HPO_4$ (1.0-3.0 g/L), the carbon feed solution contained succinic acid (80.0-100.0 g/L) and disodium succinate (40.0-60.0 g/L), and the nitrogen feed solution contained 200-300 g/L of $NH_4Cl$. The pH of all the above solutions was adjusted to 7.0.

To initiate fermentation, 35 ml sterile TES solution (solution 5) was added to the fermenter already containing sterilized solution 4. Then, 55 ml sterile phosphate solution (solution 6) was added under agitation (500 rpm) and aeration at 1 VVM (8 liters/min) and the temperature in the fermenter was established at 28° C.

The carbon feed solution (succinate solution 8) was connected to the feed pumps, followed by connecting solution 7 (antifoam solution) to the feed pumps. The growth medium's pH was adjusted to pH 7 with sterile NaOH 10N (solution 9) and sterile succinate solution as required. The DO (dissolved oxygen) electrode was calibrated.

The bacteria inoculum was added to the fermenter using feed pump. The cell concentration was 2.3-3.2 OD/L. Finally, the phosphate solution (solution 6) and ammonium chloride solution (solution 3) were connected to the feed pumps.

During the fed-batch fermentation the temperature was kept within a minimum of 25° C. and maximum of 31° C. and the oxygen level was kept at or below 10%. The pH was controlled between minimum 6.8 and maximum 7.3. Succinate solution was added whenever the pH increased above 7.1. NaOH 10N (solution 9) was added whenever the pH decreased below 6.8.

After 16 hours of fermentation, the nitrogen supply and the phosphorous supply to the growth medium were renewed by pumping 80 ml of solution 3 ($NH_4Cl$ 5N) via a peristaltic pump (pump velocity 1 ml/min) and 20 ml solution 6 (phosphate solution) into the fermenter. Then, 90 ml $NH_4Cl$ were added every 12 hours period, and 20 ml phosphate were added (pumped in) every 24 hours period. The ammonia and phosphorous levels were monitored during fermentation and addition of solutions 3 and 6 depended on the analysis results of this monitoring.

Carbon supply was renewed by addition of succinic acid (solution 8) whenever the level of succinic acid in the growth medium reduced to 1-2 g/L. The oxygen level was kept at or below 10% after about 10-20 hours of fermentation. This level of oxygen speeds up bacteriochlorophyll production.

The initial volume of the growth medium was about half of the volume of the bioreactor. Fermentation continued for up to 120 hours, and the volume increased to about full bioreactor capacity.

Example 4

Extraction of Bacteriochlorophyll a

After completion of the fermentation, the bacteria were removed by centrifugation at 4500 rpm for 15 minutes, and the culture supernatant was discarded. The immersed cells were lyophilized. Bchla was extracted from the dry (lyophilized) cells using methanol. The yield of Bchla was 0.15-0.3 gr/Liter.

What is claimed is:

1. A method of fed-batch fermentation for production of bacteriochlorophyll a (Bchla) from *Rhodovulum sulfidophilum*, said method comprising:
   (i) culturing cells of *Rhodovulum sulfidophilum* in a fermenter vessel in a growth medium comprising citric acid, $CaCl_2*2H_2O$, $MgSO_4*7H_2O$, $FeNH_4$citrate, succinic acid, disodium succinate*$6H_2O$ $Na_2SO_4$, $K_2CO_3$, yeast extract, $NH_4Cl$, $KH_2PO_4$,$K_2HPO_4*3H_2O$, NaCl, NaOH, KOH, an anti-foam agent and trace elements;
   (ii) submitting the culture to a fed-batch fermentation while feeding to the medium a succinate carbon source, an inorganic compound nitrogen source and a phosphorous source from external reservoirs connected to the fermenter vessel and keeping the oxygen level at or lower than 10%;
   (iii) removing the cells from the medium; and
   (iv) separating and recovering Bchla from the cells from said (iii).

2. The method according to claim 1, wherein in step (ii) said succinate carbon source is an aqueous solution of succinic acid and disodium succinate; said inorganic compound nitrogen source is an aqueous solution of $NH_4Cl$; and said phosphorous source is an aqueous solution of $KH_2PO_4$ and $K_2HPO_4*3H_2O$.

3. The method according to claim 1, wherein the growth medium is prepared as follows:
   (a) forming in the fermenter vessel an initial fermentation medium by preparing a culturing solution by adding to an aqueous solution of citric acid, $CaCl_2*2H_2O$, $MgSO_4*7H_2O$ and $FeNH_4$citrate an aqueous solution of succinic acid, $Na_2SO_4$, $K_2CO_3$ and yeast extract, followed by addition of NaCl, mixing, and addition of a solution of $NH_4Cl$, and adjusting the pH to 5 using 10N NaOH, followed by adding to the culturing solution an aqueous solution of an anti-foam agent, closing the fermenter and sterilizing by autoclaving, and further adding to the sterile medium an aqueous solution of the trace elements $CoCl_2*6H_2O$, $NiCl_2*6H_2O$, $CuCl_2*2H_2O$, $MnCl_2*4H_2O$, $ZnSO_4*7H_2O$, $Na_2MoO_4*2H_2O$, $H_3BO_3$ and KI, followed by addition of an aqueous solution of the phosphate salts $KH_2PO_4$ and $K_2HPO_4*3H_2O$;

(b) after addition of an inoculum of *Rhodovulum sulfidophilum* to the initial fermentation medium of (a), further providing during fermentation the succinate carbon source, the ammonium chloride nitrogen source and the phosphate source to the fermentation medium as needed.

4. The method according to claim 3, comprising:
(i) forming the culturing solution in the fermenter vessel, and adjusting the pH to 5 using NaOH;
(ii) calibrating the pH electrode and connecting to the fermenter vessel the pH electrode and the DO electrode;
(iii) adding to the culturing solution an aqueous solution of an anti-foam agent;
(iv) closing the fermenter and sterilizing the medium by autoclaving;
(v) adding to the sterile medium an aqueous solution of the trace elements $CoCl_2*6H_2O$, $NiCl_2*6H_2O$, $CuCl_2*2H_2O$, $MnCl_2*4H_2O$, $ZnSO_4*7H_2O$, $Na_2MoO_4*2H_2O$, $H_3BO_3$ and KI, followed by addition of an aqueous solution of the phosphate salts $KH_2PO_4$ and $K_2HPO_4*3H_2O$;
(vi) under agitation and aeration connecting the succinate solution and the antifoam solution to the feed pumps;
(vii) establishing a temperature of 28° C. in the fermenter and adjusting the pH to 7 with NaOH and succinate solution as required;
(viii) adding an inoculum of *Rhodovulum sulfidophilum* to the fermenter;
(ix) connecting the aqueous solution of the phosphate salts $KH_2PO_4$ and $K_2HPO_4*3H_2O$ and the ammonium chloride solution to the feed pumps;
(x) proceeding to fermentation while monitoring the temperature, the pH, the oxygen level and the supply of nitrogen, carbon and phosphorus; and
(xi) continuing the fermentation until the volume of the fermentation medium in the vessel increases to about its full capacity.

5. The method according to claim 4, wherein in said (x) the temperature is maintained at a minimum of 25° C. and a maximum of 31° C.; the pH control limits are 6.8 and 7.3; the oxygen level is 10% or less after 10-20 hours of fermentation; and succinate carbon source, ammonium chloride and phosphate source solutions are added from the external reservoirs as needed.

6. The method according to claim 5, wherein the ammonium chloride solution is pumped after 16 hours of fermentation and then each 12 hours, and the phosphate solution is pumped after 16 hours of fermentation and then each 24 hours.

7. The method according to claim 1, wherein the trace elements are selected from the group consisting of $CoCl_2*6H_2O$, $NiCl_2*6H_2O$, $CuCl_2*2H_2O$, $MnCl_2*4H_2O$, $ZnSO_4*7H_2O$, $Na_2MoO_4*2H_2O$, $H_3BO_3$, KI and combinations thereof.

* * * * *